United States Patent
Rochat

(10) Patent No.: US 8,328,537 B2
(45) Date of Patent: Dec. 11, 2012

(54) PUMPING UNIT FOR ENTERAL OR PARENTERAL NUTRITION OR PERFUSION

(76) Inventor: Jean-Denis Rochat, Genolier (CH)

(*) Notice: Subject to any disclaimer, the term of this patent is extended or adjusted under 35 U.S.C. 154(b) by 559 days.

(21) Appl. No.: 12/531,278

(22) PCT Filed: Mar. 7, 2008

(86) PCT No.: PCT/CH2008/000094
§ 371 (c)(1),
(2), (4) Date: Sep. 14, 2009

(87) PCT Pub. No.: WO2008/110024
PCT Pub. Date: Sep. 18, 2008

(65) Prior Publication Data
US 2010/0130934 A1    May 27, 2010

(30) Foreign Application Priority Data

Mar. 12, 2007    (EP) .................................. 07405082

(51) Int. Cl.
F04B 17/00    (2006.01)
A61M 1/00    (2006.01)
(52) U.S. Cl. ..................................... 417/413.1; 604/153
(58) Field of Classification Search .................. 417/412, 417/413.1, 415, 416, 417, 477.2; 604/67, 604/151, 152, 153
See application file for complete search history.

(56) References Cited

U.S. PATENT DOCUMENTS

| | | | | |
|---|---|---|---|---|
| 3,976,402 A | * | 8/1976 | Lundquist | 417/566 |
| 4,181,245 A | * | 1/1980 | Garrett et al. | 222/450 |
| 4,303,376 A | | 12/1981 | Siekmann | |
| 4,336,800 A | * | 6/1982 | Pastrone | 604/141 |
| 4,557,725 A | * | 12/1985 | Heyne et al. | 604/67 |
| 4,768,547 A | | 9/1988 | Danby et al. | |
| 4,927,411 A | * | 5/1990 | Pastrone et al. | 604/65 |
| 5,575,632 A | * | 11/1996 | Morris et al. | 417/477.2 |

(Continued)

FOREIGN PATENT DOCUMENTS

| | | |
|---|---|---|
| EP | 0223580 B1 | 5/1987 |
| EP | 1400254 A1 | 3/2004 |
| EP | 1967223 A1 | 9/2008 |

(Continued)

OTHER PUBLICATIONS

International Search Report of PCT/CH2008/00094, Mailing Date of Sep. 3, 2008.

*Primary Examiner* — Peter J Bertheaud
(74) *Attorney, Agent, or Firm* — Westerman, Hattori, Daniels & Adrian, LLP

(57) ABSTRACT

A single-use pumping casing (A) includes an inlet duct (6), a delivery duct (7) and a alternating-movement pumping member (1a), and a driving mechanism including a member (4) for driving the pumping member (1a) in at least one of the alternating movements thereof. The driving mechanism is housed in a holder housing (B) having a wall with a retaining slideway (19) for engaging sliding members of the pumping casing (A), the housing further including a passage opening (21) for the driving member (4), an abutment (20) for determining the position of the pumping casing (A) along the retaining slideway (19) and for placing the pumping member (1a) into a drive relation with the driving member (4), and a removable attachment (19, 20) for attaching the pumping casing (A) in the determined position along the retaining slideway (19).

9 Claims, 2 Drawing Sheets

U.S. PATENT DOCUMENTS

| | | | |
|---|---|---|---|
| 5,601,420 A * | 2/1997 | Warner et al. | 417/474 |
| 5,647,852 A | 7/1997 | Atkinson | |
| 7,258,534 B2 | 8/2007 | Fathallah et al. | |
| 2007/0166181 A1 | 7/2007 | Nilson | |
| 2008/0038130 A1 | 2/2008 | Fathallah et al. | |
| 2008/0039824 A1 | 2/2008 | Fathallah et al. | |

FOREIGN PATENT DOCUMENTS

| | | |
|---|---|---|
| GB | 2053378 A | 2/1981 |
| WO | 03075984 A1 | 9/2003 |
| WO | 2005030299 A1 | 4/2005 |

\* cited by examiner

PUMPING UNIT FOR ENTERAL OR PARENTERAL NUTRITION OR PERFUSION

BACKGROUND ART

The present invention relates to a pumping unit for enteral, parenteral or infusion feeding, comprising a single-use pumping chamber provided with an inlet duct, a delivery duct and an elastically deformable pumping membrane, a pusher for alternately deforming the deformable membrane, said driving pusher being housed in a support casing one wall of which has a retaining slideway with which the sliding elements of the pumping chamber engage, this support casing also having a through-opening for the driving pusher, and abutment means for determining the position of the pumping chamber along the retaining slideway and for putting said pumping membrane into drive connection with said driving pusher.

The majority of pumping units used in this type of application employ peristaltic pumps. The drawback with this type of pump is its very poor efficiency owing to friction inherent in its design. As a result, it is not possible to pump more than about 3 liters with a battery supplying around 26 000 J. This limited pumping capacity between battery recharges constitutes a major drawback which makes ambulatory use problematical.

Another drawback with these pumps results from the installation of the tubing between the tube-deforming pads or rollers and the cylindrical bearing surface of this tube with respect to which the pads or rollers are driven. The pump can only operate if the flexible tube is correctly positioned. In order to avoid the risk of incorrect installation, it is generally proposed for that part of the flexible pipe that engages with the pump rollers, and also the bearing surface against which the tube is deformed, to be provided in a cassette which has means for fastening it to the roller drive mechanism.

U.S. Pat. No. 5,647,852 proposes a piston pump in the form of a cassette comprising means for its positioning and removable fastening on a drive mechanism having a linear motor. Such a pump is used for lavage in the medical, dental and therapeutic fields.

WO 2005/030299 proposes a pumping device with a cassette provided with control and pumping membranes, where the cassette is introduced into a slideway of a carriage which is itself mounted such that it slides on a framework comprising the pumping cassette drive mechanism. Once the cassette has been installed on the carriage, the latter is pushed back toward the framework in order to put the operating membranes in contact with driving pushers.

The main drawback with this device is its complexity and thus its cost and reliability. In addition, preloading of the pumping membrane results from the carriage moving along the same course as that along which the control pusher of this membrane is moved, but in the opposite direction. Thus, if the carriage, when it has been pushed back toward the framework, is not in exactly the right position, the stroke of the membrane and thus the volume pumped will vary.

SUMMARY OF THE INVENTION

There is currently no pump for enteral, parenteral or infusion feeding on the market which is able to pump much when powered by battery. The only solutions known employ special batteries holding more than 20 000 J which are thus expensive and only allow around 3 liters to be pumped, which is too little to allow such a system to meet the requirements of ambulatory use or of being able to provide a viable alternative to conventional systems having gravity flow of liquid and a clamp-controlled flowrate. This is one of the reasons why gravity flow of liquid is still commonly used, despite its drawbacks.

It is the object of the invention to at least partly remedy the problems of the abovementioned pumping systems.

To this end, the subject of the invention is a pumping unit for enteral, parenteral or infusion feeding as claimed in claim 1.

Considering the type of pump and its drive mechanism, which preferably has a very small stroke (typically <2 mm) and preferably a high frequency (typically above 10 Hz) so as to give the pumping unit of the invention a flowrate of around 2 l/h and a long pumping time between battery recharges, it is important that the positioning of the single-use part on the drive mechanism makes cleaning and installation as easy as possible with a precision suitable for precise operation of the pumping unit.

This precision can be obtained by structural elements, namely the dimensions of the slideway holding the pumping chamber and those of this pumping chamber, which are precisely reproducible because such a pumping chamber is injection molded and the precision is provided by the mold. As far as the precision of the slideway is concerned, this is a simple milling which can itself also be produced with great precision. The fact that the slideway is in a plane perpendicular to the stroke of the driving pusher of the pumping membrane also contributes to ensuring great precision by very simple means.

BRIEF DESCRIPTION OF THE DRAWINGS

The attached drawing illustrates, diagrammatically and by way of example, an embodiment of the pumping unit according to the present invention.

DETAILED DESCRIPTION OF PARTICULAR EMBODIMENTS

The pumping unit according to the present invention comprises essentially two parts, a single-use pump A and a mechanism for driving this pump and located in a support casing B.

Figure 1:
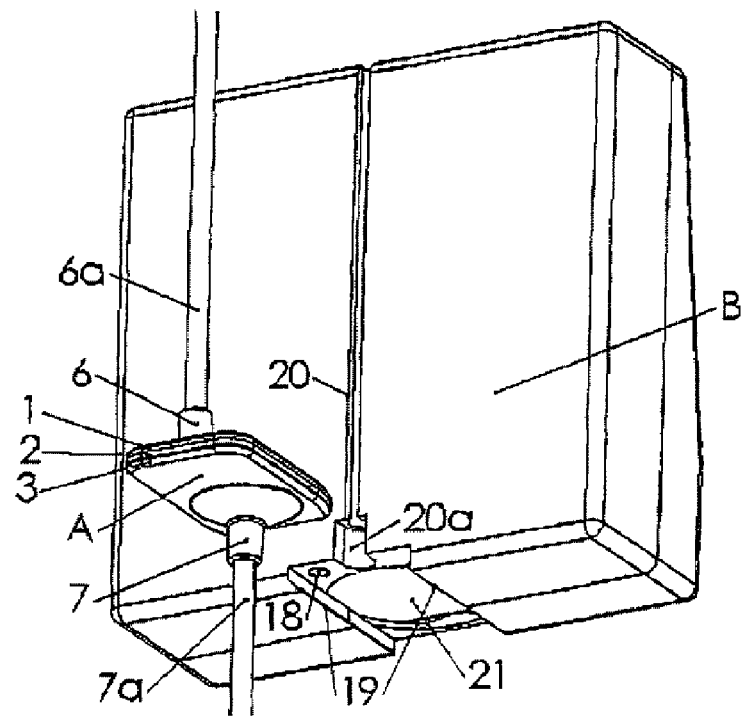
FIG. 1 is a perspective view of the two parts of the pumping unit when they are separated.
Figure 2:
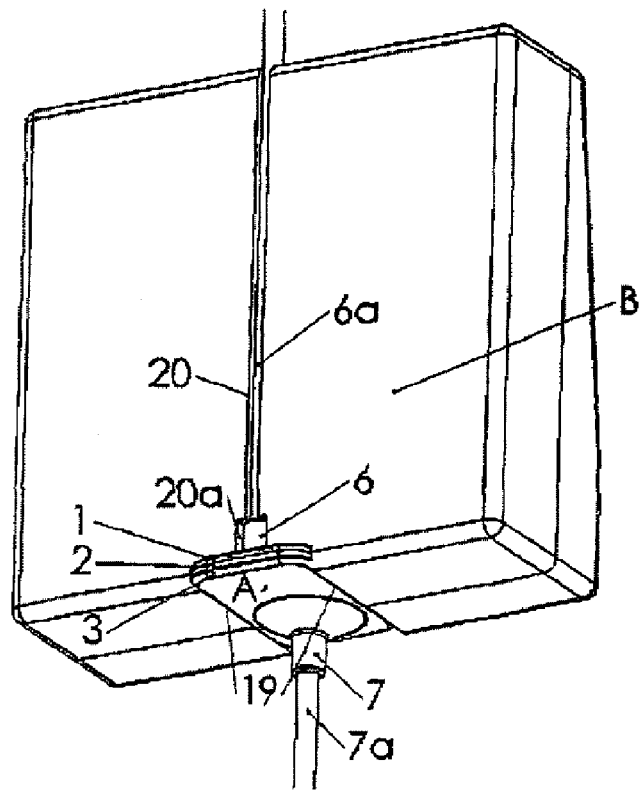
FIG. 2 is a perspective view of the two parts of the pumping unit when they are assembled.
Figure 3:
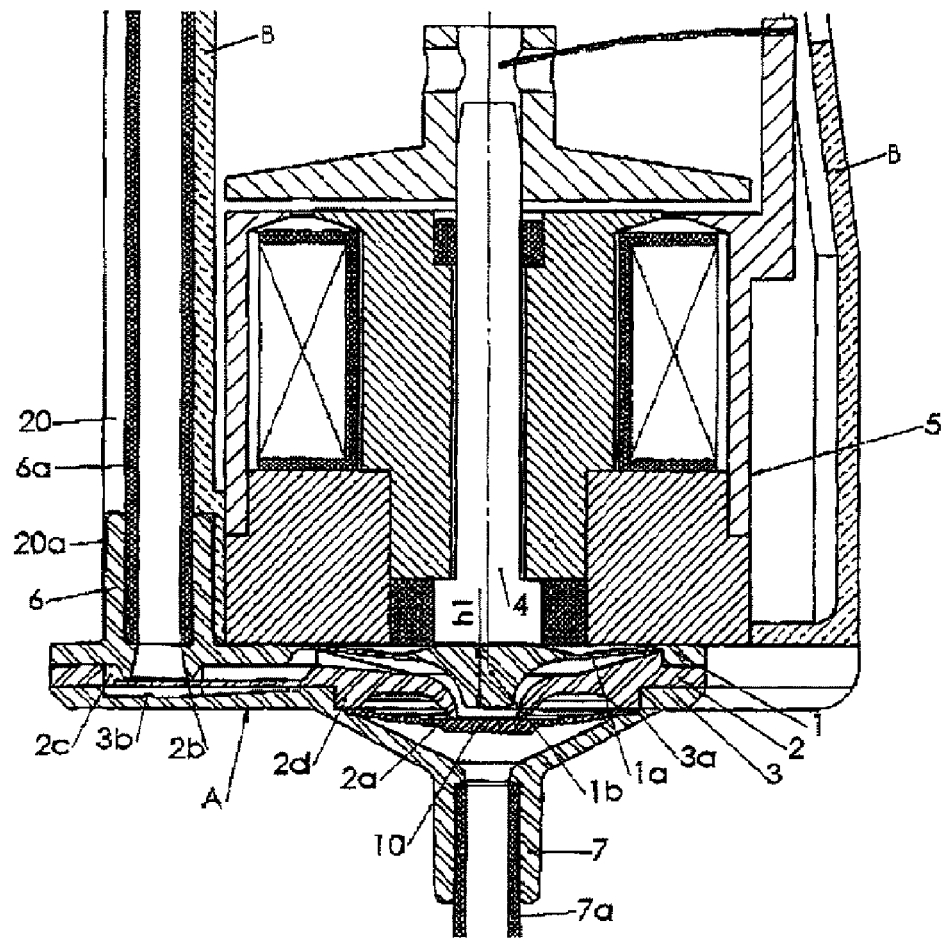
FIG. 3 is a cross-sectional view on the section line III-III in FIG. 2.

In the example illustrated, the single-use pumping chamber A is a pump of which the pumping element is an annular membrane 1a, one embodiment of which is illustrated in greater detail in FIG. 3. As can be seen, this single-use pump is formed substantially of a three-part chamber 1, 2, 3, two parts 1, 3 forming the wall of the pumping chamber and one intermediate part 2. In this example, the wall parts 1, 3 have an inlet duct 6 and a delivery duct 7 respectively. The wall part 1 has a thinner part forming an annular membrane 1a surrounding a thicker actuating part 1b. The thinner annular part 1a acts as a pumping membrane, the thicker central actuating part 1b of which is used to transmit the force exerted by a driving member to the annular membrane, said driving member in this example being a pusher formed by the moving core 4 of an electromagnet 5 driving the pump. The deformation of the membrane 1a must obviously remain within the limits of elastic deformation of the plastic forming the wall part 1.

The intermediate part 2 comprises a communication opening 2a for allowing selective communication between the upstream and downstream compartments of the pump. This communication opening 2a is located in front of the thick central part 1b of the membrane and a valve 2b is located in front of an opening 2c facing the internal end of the inlet duct 6 made in the wall part 1. The opening 2a is located at the end of a depression while the thicker central actuating part 1b forms a projection which engages in the opening 2a. The intermediate part 2 also comprises an annular projection 2d extending toward the wall part 3. Its role will be explained hereinafter.

The wall part 3 comprises a seat concentric with the delivery duct 7 in order to position a valve 10 for controlling the communication opening 2a of the intermediate part, which valve also acts as an anti-drip device so as to prevent any leakage of liquid when the single-use is not inserted in the pump. This valve 10 is located between this communication opening 2a and the delivery duct 7 of the pump. In order to prevent liquid from dripping from the pump under gravity, the valve 10 is held against the opening 2a with a pressure of $4 \times 10^4$ Pa$\pm 1 \times 10^4$ Pa.

In the rest position, it closes the opening 2a and is held against the latter as soon as the difference in pressure between the upstream and downstream sides of the communication opening 2a is less than $4 \times 10^4$ Pa$\pm 1 \times 10^4$ Pa. It separates from this opening 2a as soon as the abovementioned difference in pressure is greater than $4 \times 10^4$ Pa$\pm 1 \times 10^4$ Pa.

The wall part 3 has an annular seat 3a for positioning the valve 10. This valve 10 is held on this seat 3a by the annular projection 2d of the intermediate part 2. The wall part 3 also comprises a projection 3b located behind the control valve 2b for the inlet duct 6 in order to prevent this valve 2b being held against the internal surface of the wall part 3. As a result of this arrangement, the face of the valve 2b which is on the other side from the face next to the internal end of the inlet duct 6 of the pump is exposed to the pressure in the pump compartment located upstream of the communication opening 2a of the intermediate part 2. This valve 2b can thus close the internal end of the inlet duct 6 in the delivery phase of the pump and open it in the intake phase.

Advantageously, the above-described pump is designed to operate with a long pumping time between battery recharges. To this end, a number of conditions have been combined, both relating to the pump itself and its drive mechanism. Details relating to this pump and its drive mechanism are described in patent application EP 07405078.2, to which reference may be made for more details without this being necessary in order to understand the present invention.

First of all, as regards the pump itself, the membrane 1a has a relatively small diameter of between 3 and 25 mm, advantageously about 16 mm so as to limit its actuating force which is the product of the pressure P and the area S. Given that this membrane is preferably intended to be actuated by means of a low-consumption electromagnet, a small electromagnet has been chosen. The stroke of the membrane 1a, driven by the pusher-core 4 of the electromagnet, is preferably between 0.2 and 2 mm, advantageously around 0.5 mm. Under these conditions, the stroke of the membrane 1a allows it to be driven directly by the pusher-core 4 of the electromagnet and avoids the need for mechanical speed reduction which would substantially reduce the overall efficiency of the pump.

Advantageously, the thickness of the elastic membrane 1a is between 0.1 and 0.7 mm, preferably around 0.3 mm. These dimensions enable the use of the same thermoplastic for the membrane 1a and for the wall part 1 of the pump chamber, thus making it possible to produce the part 1 and the membrane 1a in one injection molding operation. Among the thermoplastics that can be used, mention may be made of PC, PVC, ABS, PP and PE in particular. The choice depends on the cost, the precision and the stability of the elastic properties after sterilization and storage for at most three years. PC is the best-suited material for these specifications.

In order to maximize the energy economy necessary for driving the pump, the elasticity of the membrane 1a of the pump is intended to be used to return said membrane to its rest position after it has been driven by the moving core 4 of the electromagnet 5, such that this membrane 1a must be preloaded, advantageously to around $2 \times 10^4$ Pa.

To this end, the lower surface of the support casing B of the drive electromagnet 5 has a retaining slideway 19 which extends from one side of the lower surface of the support casing B to the other and the cross-sectional profile of which may advantageously be in the form of a dovetail thus forming two sliding pads angled at about 45° so that it can engage with two parallel edges of the walls 1, 3 of the pumping chamber A, these walls constituting the sliding elements of this pumping chamber A. This retaining slideway 19 may have any other appropriate profile matched to that of the parallel edges of the walls 1, 3 of the pumping chamber A, so as to press the external surface of the wall 1 of the single-use pumping chamber A against the bottom of the retaining slideway 19 and keep it held there. As can be seen in FIG. 3, when the pumping chamber A is engaged with the slideway 19, the deformable membrane 1a is subjected to a preloading deformation in the rest position so that it is able to use its own elasticity to return sufficiently quickly to its rest position after it has been moved by the pusher-core 4 of the electromagnet 5.

Figure 4:
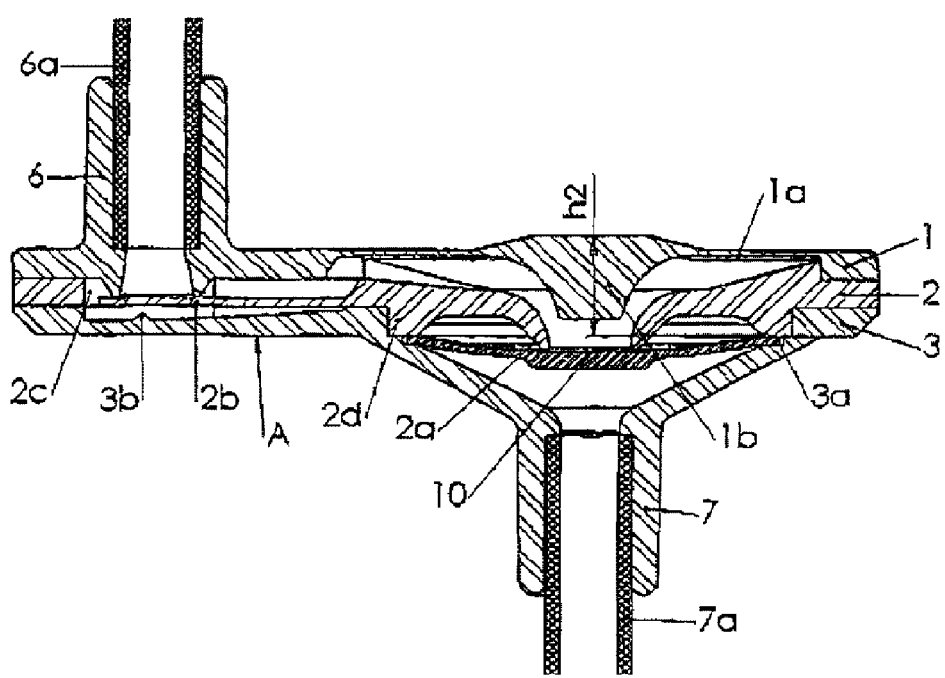
FIG. 4 is a cross-sectional view through the single pumping chamber illustrated in FIG. 3, with the pumping membrane unloaded.

By comparing the preloaded deformable membrane 1a in FIG. 3 with that of FIG. 4 where the deformable membrane 1a is unloaded, it can be seen that the difference between the height $h_2$ of the membrane 1a in FIG. 4 and the height $h_2$ of the same membrane in the preloaded state in FIG. 3 gives the preload value. This preload results exclusively from the difference between the depth of the slideway 19 which corresponds to $h_1$ and the height $h_2$ which corresponds to that part of the height of the pumping chamber A which is installed in the slideway 19. This preload and also the precision of the stroke of the deformable membrane 1a brought about by the pusher 4 are thus exclusively provided by the structural dimensions and not by the precision of the stroke of the pumping chamber A in the slideway 19.

Simply introducing the pumping chamber A into the slideway 19 ensures perfectly reproducible precision. In addition, the slideway constitutes an element that is easily accessible and visible, which means that it can be kept clean and ensures long-lasting precision over time.

A communication opening 21 is made in the base of the retaining slideway 19 in order for the pusher-core 4 of the electromagnet 5 to engage with the thicker central part 1b of the pumping chamber A. It can also be seen that the retaining slideway 19 passes from one side of the lower wall of the support casing B to the other, thereby facilitating cleaning since this retaining slideway is open to the outside at both ends and there are no recesses in which dust could accumulate.

The single-use pumping chamber A is positioned and held in the retaining slideway 19 by clipping the flexible intake duct 6a of the single-use pumping chamber A into a channel 20 made in a wall of the support casing B next to the lower wall in which the retaining slideway is made. The width of the longitudinal opening thereof, which provides access to this channel 20, is slightly narrower than the diameter of the duct 6a, such that a slight elastic deformation of the cross section of this duct 6a is necessary in order to introduce it into the channel 20, after which the cross section of the flexible duct 6a resumes its initial shape, ensuring that the pumping chamber A is held in the retaining slideway 19 and the thicker central part 1b of the membrane 1a is positioned opposite the pusher-core 4 of the electromagnet 5. The bottom of the channel 20 has a part 20a with a larger diameter for holding the part 6 of the inlet duct which is fixed to the pump A.

To prevent wear of the sliding pads of the retaining slideway 19, the plastic of the support casing B can advantageously be reinforced with glass beads having a size of 50 µm to 500 µm. This reinforcement also protects the support casing from being scratched.

An ON-OFF switch 18 is provided in the base of the slideway 19 so that the electromagnet 5 can only be switched on when the pump A has been inserted into the slideway 19. This puts the electromagnet 5 into the ready-to-pump mode. The user can then input pump control parameters by means of a control station (not shown). This switch 18 could also be located in the channel 20 or in the widened part 20a thereof, and this would have the same effect of putting the electromagnet into the ready-to-pump mode when the pump A is installed.

The invention claimed is:

1. A pumping unit for enteral, parenteral or infusion feeding, comprising:
   a single-use pumping chamber provided with an inlet duct, a delivery duct, and an elastically deformable pumping membrane,
   a driving pusher for alternately deforming the elastically deformable pumping membrane, said driving pusher being housed in a support casing, the support casing comprising a first wall with a retaining slideway disposed therein, sliding elements of the pumping chamber engaging said retaining slideway,
   said support casing further comprising a through-opening for the driving pusher and an abutment means for determining an installed position of the pumping chamber within the retaining slideway and for putting a contact surface of said elastically deformable pumping membrane into contact with said driving pusher,
   the driving pusher having a stroke between a rest position in which the membrane is in a rest position and a maximum actuating position in which the membrane is under maximal load,
   wherein when said pumping chamber is in said installed position within the retaining slideway said contact surface of the elastically deformable pumping membrane is spaced from an exposed end surface of the pumping chamber by a first distance, and when said pumping chamber is in an uninstalled position said contact surface of the elastically deformable pumping membrane is spaced from said exposed end surface of the pumping chamber by a second distance, and
   wherein said first distance is smaller than said second distance such that installing the pumping chamber in the retaining slideway automatically puts the elastically deformable pumping membrane under a predetermined preload even with the driving pusher in the rest position.

2. The pumping unit as claimed in claim 1, further comprising a means for removably fastening said pumping chamber in said installed position within the retaining slideway.

3. The pumping unit as claimed in claim 1, wherein a second wall of the support casing adjacent to the first wall with the retaining slideway has a clip-in channel in which the inlet duct is clipped, said clip-in channel defining the lateral position of said elastically deformable pumping membrane with respect to the driving pusher and serving as a means for removably fastening the pumping chamber within the retaining slideway.

4. The pumping unit as claimed in claim 1, wherein an ON-OFF switch for putting a pump drive mechanism into a ready-to-pump mode is located on the support casing at a location where it can be actuated by the installation of the pumping chamber in the retaining slideway.

5. The pumping unit as claimed in claim 2, wherein a second wall of the support casing adjacent to the first wall with the retaining slideway has a clip-in channel in which the inlet duct is clipped, said clip-in channel defining the lateral position of said elastically deformable pumping membrane with respect to the driving pusher and serving as the means for removably fastening the pumping chamber within the retaining slideway.

6. The pumping unit as claimed in claim 2, wherein an ON-OFF switch for putting a pump drive mechanism into a ready-to-pump mode is located on the support casing at a location where it can be actuated by the installation of the pumping chamber in the retaining slideway.

7. The pumping unit as claimed in claim 3, wherein an ON-OFF switch for putting a pump drive mechanism into a ready-to-pump mode is located on the support casing at a location where it can be actuated by the installation of the pumping chamber in the retaining slideway.

8. The pumping unit as claimed in claim 5, wherein an ON-OFF switch for putting a pump drive mechanism into a ready-to-pump mode is located on the support casing at a location where it can be actuated by the installation of the pumping chamber in the retaining slideway.

9. The pumping unit as claimed in claim 1, wherein a cross-sectional profile of the retaining slideway is in the form of a dovetail, thus forming two sliding pads angled at about 45° so that the retaining slideway can engage with two parallel edges of walls of the pumping chamber, said walls of the pumping chamber constituting the sliding elements.

* * * * *